(12) United States Patent
Kong

(10) Patent No.: US 6,616,951 B1
(45) Date of Patent: Sep. 9, 2003

(54) FERMENTED HERBAL DRINK

(76) Inventor: Jack Kong, 179 Parklawn Road, Toronto Ontario (CA), M8Y 3J2

( * ) Notice: Subject to any disclaimer, the term of this patent is extended or adjusted under 35 U.S.C. 154(b) by 0 days.

(21) Appl. No.: 10/150,361

(22) Filed: May 20, 2002

(51) Int. Cl.$^7$ .............................................. A61K 35/78
(52) U.S. Cl. ...................................... 424/725; 424/773
(58) Field of Search .................................. 424/725, 773

(56) References Cited

U.S. PATENT DOCUMENTS 5,466,452 A * 11/1995 Whittle ........................ 424/725
6,060,063 A * 5/2000 Lansky ........................ 424/776

OTHER PUBLICATIONS

Computer ABS CN1190589 Guantianying et al "Complex Ferrous Sulfate Tablet"Pub Aug. 1998.*
Computer ABS CN 1266892 WU HONGFEI "Health–Care Orange Wine" Pub Sep. 2000.*
Computer ABS Web Site: www.rain–tree.com/dongquai—"Dang Gui; Dong Quai" May 12, 2003.*
Computer ABS Web Site: http://dreampharm.com/garlic/angelic "All About Dang Gui" May 12, 2003.*

* cited by examiner

*Primary Examiner*—Herbert J. Lilling
(74) *Attorney, Agent, or Firm*—Elias C. Borges

(57) ABSTRACT

An herbal extract which is effective in treating the symptoms of menopause is disclosed. The herbal extract comprises an aqueous suspension of a plurality of fermentation products of the herb *Angelica sinensis*. The suspension is made by suspending a quantity of crushed *Angelica sinensis* with a quantity of active yeast in a volume of water and then permitting the yeast to ferment the crushed *Angelica sinensis*. The fermentation is preferably carried out at a temperature selected for optimum fermentation period of at least seven days. The optimum fermentation temperature is preferably between 10° C. to 20° C. The fermented mixture may then be filtered after the end of the fermentation period to remove a majority of any coarse solids remaining in the suspension. A yeast nutrient mixture may also be added to the suspension prior to fermentation. Preferably, the fermentation period is less than 30 days.

7 Claims, 1 Drawing Sheet

FERMENTED HERBAL DRINK

FIELD OF THE INVENTION

The invention relates generally to herbal drinks.

BACKGROUND OF THE INVENTION

Traditional medicine often incorporates a variety of herbal remedies to treat or prevent a variety of ailments. Ginseng, St. John's Wort, and Chinese Angelica are three examples of herbs which have been used for centuries to treat a variety of ailments. Chinese Angelica (*Angelica sinensis*), for example, has been used in traditional Chinese medicine as a menstrual cycle balancer for treating all menstrual disturbances including menstrual pain. In addition to treating particular ailments, many herbs are consumed to help promote vitality and good health. Chinese Angelica, for example, has been used in traditional Chinese medicine as a primary female tonic having nutritive and restorative effect.

Herbal remedies may be administered in a variety of forms. Certain herbs can be consumed whole as a food ingredient. Herbs such as Ginseng and Licorice root are often made into tea. Increasingly, herbs are consumed as dried powders or liquid extracts. Powdered herbs are often sold in the form of capsules or pills, while liquid extracts are often sold as tinctures and tonics. Herbal extracts can be made by extraction of the herb with either aqueous or alcohol solutions. Since any herb will contain a variety of different chemical compounds, different extraction techniques will result in extracts having different chemical compositions. Aqueous extraction techniques are more effective in extracting hydrophilic (i.e. water soluble) compounds rather than hydrophobic (i.e. non-water soluble) compounds from herbs. Conversely, alcohol extraction techniques are generally better able to extract hydrophobic compounds. Therefore, an aqueous extract of a particular herb may have a very different chemical composition than an alcohol extract of the same herb. Since a particular herb may have a variety of different chemical compounds which have a medicinal effect, the more active compounds the extract has, the more effective the extract may be. This is particularly true if the extract is to be used as a tonic, since tonics are taken to provide multiple medical and quasi-medical benefits. Unfortunately, presently available extracts of Chinese Angelica are not as effective as possible because they lack some of beneficial compounds found in the fresh herb.

SUMMARY OF THE INVENTION

In accordance with the present invention, there is provided an improved herbal extract for use as a tonic comprising an aqueous suspension of the fermentation products of Chinese Angelica.

In accordance with another aspect of the present invention, there is provided a method of manufacturing an herbal extract comprising the steps of combining a quantity of Chinese Angelica with a quantity of water and a quantity of active yeast followed by fermenting the Chinese Angelica.

With the foregoing in view, and other advantages as will become apparent to those skilled in the art to which this invention relates as this specification proceeds, the invention is herein described by reference to the accompanying drawings forming a part hereof, which includes a description of the preferred typical embodiment of the principles of the present invention.

DESCRIPTION OF THE DRAWINGS

In the drawings like characters of reference indicate corresponding parts in the different figures.

DETAILED DESCRIPTION OF THE INVENTION

Figure 1:
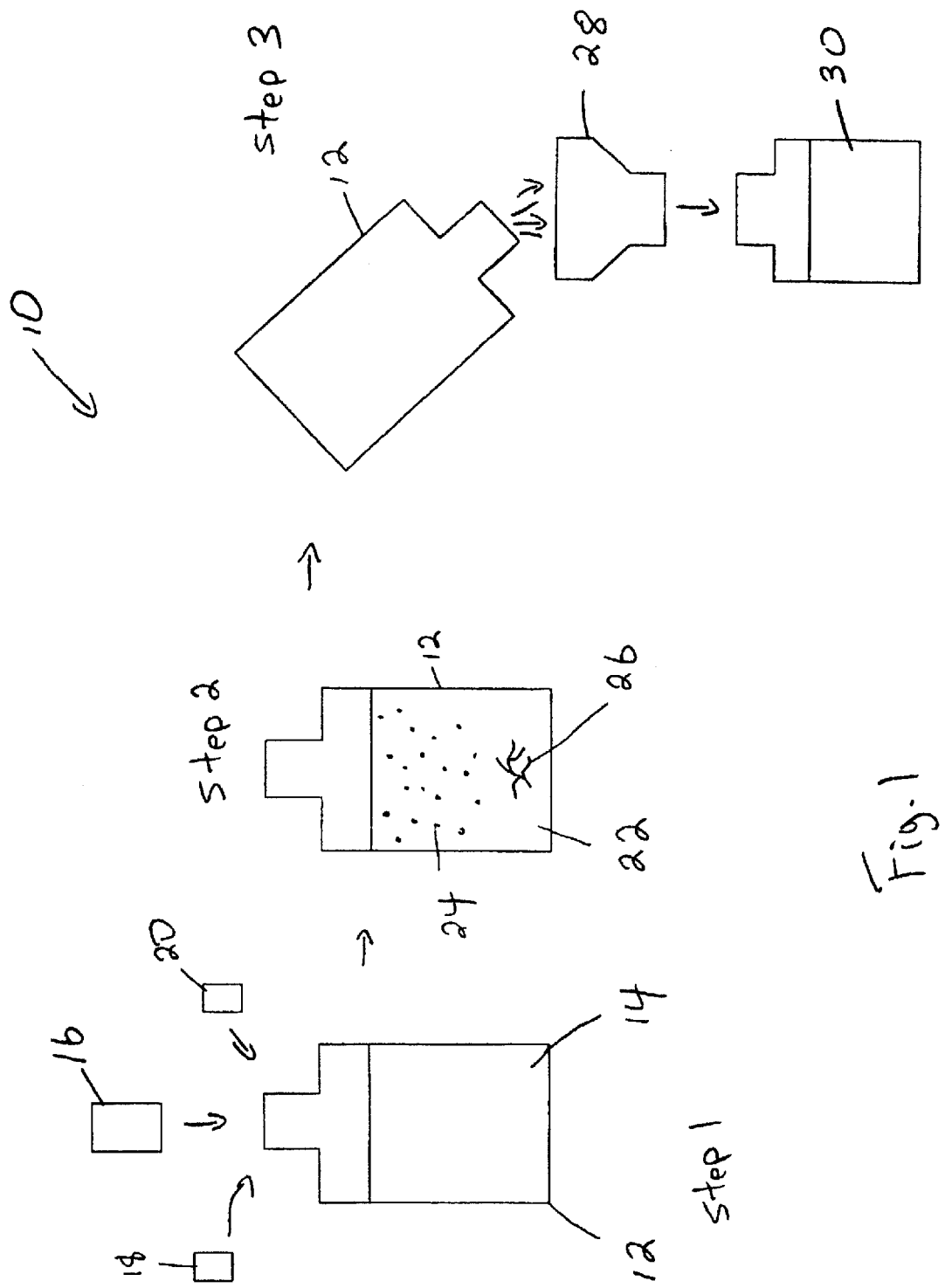
FIG. 1 is a schematic representation of method of the present invention.

The present invention is a herbal extract useful for the treatment of menopausal women comprising an aqueous suspension of the fermentation products of the herb Chinese Angelica. It has been discovered that this particular extract is more effective than alcohol or aqueous extracts of Chinese Angelica. A method of manufacturing the herbal extract is show schematically in FIG. 1. Essentially the method comprises the steps of combining a quantity of Chinese Angelica 16 with active yeast 18 in a fermentation vessel 12 having water 14. The quantity of Chinese Angelica used in the present method can be either fresh or dried. Better fermentation will result if the fresh herb is used. Preferably, the herb is first crush before placing it in fermentation vessel 12 in order to increase the rate of fermentation. Also, it is preferable to use only the roots of the herb in making the extract. If fresh Chinese Angelica is not available, dried Chinese Angelica may be used; however, a quantity of yeast nutrients 20 may have to be added in order to promote and maintain the fermentation process. Since the fresh herb has more nutritive value than the dried herb, the fresh herb is likely to require little or no nutritive supplements in order to maintain fermentation. There are a variety of yeast nutrient supplements on the market today.

After the ingredients have been mixed in fermentation vessel 12, the mixture is permitted to ferment for a period time, generally between seven days to no more than thirty days. It has been discovered that a minimum of seven day is required before the Chinese Angelica contained in the mixture ferments sufficiently to release an effective concentration of medicinal and quasi-medicinal compounds into solution. During the fermentation process, mixture 22 is held in conditions conducive to fermentation. In particular, the temperature of mixture 22 should be held at or close to an optimal fermentation temperature. The optimal fermentation temperature may vary depending on the yeast used in the mixture. Generally speaking, any active yeast used in the fermenting of beer or wine can be used. Preferably, mixture 22 is held at a temperature of between 10 degrees centigrade to 20 degrees centigrade, again depending on the variety of yeast used.

Fermentation vessel 12 should also be held in a substantially sterile environment to prevent mixture 22 from being contaminated by bacteria or other microorganisms which may interfere with the fermentation process. Standard fermentation techniques as used in the wine and beer industry can be used to maintain the sterile conditions. It has been discovered that in most cases the fermentation will be substantially completed after 21 days. While mixture 22 may be permitted to ferment further, the longer the mixture is permitted to ferment, the greater the probability that the mixture will be contaminated. It has been discovered that if mixture 22 is permitted to ferment for more than 30 days, the quality of the final product deteriorates.

After mixture 22 has been permitted to ferment for the desired fermentation period, the solid components should be separated from the mixture. Essentially there will be two types of solid components suspended in mixture 22, namely fine particulate matter 24 and coarse solids 26. Coarse solids 26 will consist of those portions of the herb which could not be broken down via the fermentation process. The third step in the process, therefore, involves passing solution 22 through a filter 28 to remove the coarse solids. Depending on the fineness of filter 28, a majority of the fine particulate matter 24 may also be removed. The finished product 30 may then be consumed by itself as a tonic, or it may be mixed with fruit juices to form an invigorating healthful drink.

The herbal extract made in accordance with the method of the present invention has been discovered to have better efficacy than standard aqueous or alcohol extractions of Chinese Angelica. Both aqueous and alcohol extraction techniques only release a small proportion of the beneficial compounds contained in the herb. It is believed that Chinese Angelica contains a plurality of beneficial chemical compounds either bonded to or in close association with various sugar and starch molecules within the tissues of the herb. In the fermentation process, the yeasts contained in the fermentation solution release enzymes into the solution which break down these sugar and starch molecules. The yeast converts the sugars to alcohol and, in the process, releases the beneficial chemical compounds trapped in the herb tissues. It is believed that the break down of the sugars during fermentation actually cause the beneficial compounds associated with these molecules to be freed. Therefore, during the course of fermentation, a different series of chemical compounds are released into solution from the herb. The resulting solution is not only more palatable than traditional alcohol or aqueous extracts, but it is actually more effective. In particular, it has been discovered that the fermented extract is useful in alleviating the systems of menopause, a result which is not observed with either the aqueous or alcohol extracts or even the whole herb. Indeed, while Chinese Angelica has been used by traditional Chinese medicine to treat menstrual pain and to regulate menstrual cycles, it has not been used in the past to alleviate the systems of menopause. It is believe that the chemical compounds released from the herb as a result of the fermentation process are effective in alleviating the systems of menopause.

A specific embodiment of the present invention has been disclosed; however, several variations of the disclosed embodiment could be envisioned as within the scope of this invention. It is to be understood that the present invention is not limited to the embodiments described above, but encompasses any and all embodiments within the scope of the following claims.

Therefore, what is claimed is:

1. An herbal extract comprising an aqueous suspension of a plurality of fermentation products of *Angelica sinensis*.

2. An herbal extract as defined in claim 1 wherein the suspension is made by suspending a quantity of crushed *Angelica sinensis* with a quantity of active yeast in a volume of water and then permitting the yeast to ferment the crushed *Angelica sinensis*.

3. An herbal extract as defined in claim 2 wherein the fermentation is carried out an optimum fermentation temperature for a fermentation period of at least seven days.

4. An herbal extract as defined in claim 3 further comprising the step of filtering the suspension after the end of the fermentation period to remove a majority of any coarse solids which have not dissolved.

5. An herbal extract as defined in claim 3 wherein the optimum fermentation temperature is between 10° C. to 20° C.

6. An herbal extract as defined in claim 2 wherein a yeast nutrient mixture is added to the suspension prior to fermentation.

7. An herbal extract as defined in claim 2 wherein the fermentation period is less than 30 days.

\* \* \* \* \*